US008742145B2

(12) United States Patent
Takumi et al.

(10) Patent No.: US 8,742,145 B2
(45) Date of Patent: Jun. 3, 2014

(54) METHOD FOR MANUFACTURING AN EPOXY COMPOUND AND METHOD FOR EPOXIDIZING A CARBON—CARBON DOUBLE BOND

(75) Inventors: Kiyoshi Takumi, Tsukuba (JP); Naoki Sasagawa, Tsukuba (JP); Yoichiro Ezaki, Tsukuba (JP); Yoshihiro Kon, Tsukuba (JP); Yutaka Ono, Tsukuba (JP); Kazuhiko Sato, Tsukuba (JP)

(73) Assignees: Arakawa Chemical Industries, Ltd., Osaka (JP); National Institute of Advanced Industrial Science and Technology, Tokyo (JP)

( * ) Notice: Subject to any disclaimer, the term of this patent is extended or adjusted under 35 U.S.C. 154(b) by 83 days.

(21) Appl. No.: 13/381,018

(22) PCT Filed: Jul. 16, 2010

(86) PCT No.: PCT/JP2010/062085
§ 371 (c)(1),
(2), (4) Date: Dec. 27, 2011

(87) PCT Pub. No.: WO2011/010614
PCT Pub. Date: Jan. 27, 2011

(65) Prior Publication Data
US 2012/0108830 A1    May 3, 2012

(30) Foreign Application Priority Data

Jul. 24, 2009 (JP) ................................ 2009-172647
Sep. 9, 2009 (JP) ................................ 2009-207625
Sep. 28, 2009 (JP) ................................ 2009-221992
Jan. 8, 2010 (JP) ................................ 2010-002585

(51) Int. Cl.
C07D 301/12    (2006.01)

(52) U.S. Cl.
USPC ........................................................ 549/531

(58) Field of Classification Search
USPC ........................................................ 549/531
See application file for complete search history.

(56) References Cited

U.S. PATENT DOCUMENTS

| 5,274,140 | A | 12/1993 | Venturello et al. | |
| 7,557,059 | B2 * | 7/2009 | Hori et al. | 502/160 |
| 2007/0117993 | A1 | 5/2007 | Hori et al. | |

FOREIGN PATENT DOCUMENTS

| JP | 55-129276 A | 10/1980 |
| JP | 55-149271 A | 11/1980 |
| JP | 56-18972 A | 2/1981 |
| JP | 62-230778 A | 10/1987 |
| JP | 6-213919 A | 8/1993 |
| JP | 6-237392 A | 9/1993 |
| JP | 2001-523281 A | 11/2001 |
| JP | 2002-80557 A | 3/2002 |
| JP | 2002-155066 A | 6/2002 |
| JP | 2003-192680 A | 7/2003 |
| JP | 2003-238544 A | 8/2003 |
| JP | 2003-300971 A | 10/2003 |
| JP | 2004-59573 A | 2/2004 |
| JP | 2004-59575 A | 2/2004 |
| JP | 2004-115455 A | 4/2004 |
| JP | 2005-169363 A | 6/2005 |
| WO | WO 98/50376 A1 | 11/1998 |
| WO | WO 2005/095370 A1 | 10/2005 |

OTHER PUBLICATIONS

Battioni et al., Monooxygenase-like Oxidation of Hydrocarbons . . . , J. Am. Chem. Soc., vol. 110, pp. 8462-8470 (1988).
Bombarda et al., Synthese de composes oxygenes derives du caryophyllene, Bull Soc. Chim Fr, vol. 132, pp. 836-842 (1995) (with English Abstract).
Dimitrov et al. The Ozonolysis of Longifolene: A Tool for the Preparation of Useful Chiral Compounds, Configuration Determination of New Stereogenic Centers by NMR Spectroscopy and X-Ray Crystallography, Helvetica Chimica Acta, vol. 86, pp. 106-121 (2003).
Hermann et al., Methyltrioxorhenium/pyrazole—A highly efficient catalyst for the epoxidation of olefins, Journal of Organometallic Chemistry, vol. 555, pp. 293-295 (1998).
Ishii et al., Hydrogen Peroxide Oxidation Catalyzed by Heteropoly Acids Combined with Cetylpyridinium Chloride: Epoxidation of Olefins and Allylic Alcohols, Ketonization of Alcohols and Diols, and Oxidative Cleavage of 1,2-Diols and Olefins, J. Org. Chem., vol. 53, pp. 3587-3593 (1988).
Sakaguchi et al., Selective Oxidation of Monoterpenes with Hydrogen Peroxide Catalyzed by Peroxotungstrophosphate (PCWP), J. Org. Chem., vol. 61, pp. 5307-5311 (1996).
Saladino et al., A novel and efficient catalytic epoxidation of olefins and monoterpenes with microencapsulated Lewis base adducts of methyltrioxorhenium, Tetrahedron, vol. 61, pp. 1069-1075 (2005).
Sato et al., A Haiide-Free Method for Olefin Epoxidation with 30% Hydrogen Peroxide, Bull. Chem. Soc. Jpn., vol. 70, pp. 905-915 (1997).
Venturello et al., Quaternary Ammonium Tetrakis (diperoxotungsto)phosphates(3-) as a New Class of Catalyst for Efficient Alkene Epoxidation with Hydrogen Peroxide, J. Org. Chem., vol. 53, pp. 1553-1557 (1998).
Villa et al., A Heterogeneous Tungsten Catalyst for Epoxidation of Terpenes and Tungsten-Catalyzed Synthesis of Acid-Sensitive Terpene Epoxides, J. Org. Chem., vol. 84, pp. 7267-7270 (1999).
International Search Report for PCT/JP2010/062085, mailed on Oct. 26, 2010.

* cited by examiner

Primary Examiner — Taylor Victor Oh
(74) Attorney, Agent, or Firm — Birch, Stewart, Kolasch & Birch, LLP

(57) ABSTRACT

The present invention provides a method for producing an epoxy compound, comprising oxidizing a carbon-carbon double bond of an organic compound by hydrogen peroxide in the presence of a neutral inorganic salt and a mixed catalyst of a tungsten compound (a), at least one phosphorus compound selected from the group consisting of phosphoric acids, phosphonic acids, and salts thereof (b) and a surfactant (c), and an epoxidizing method comprising oxidizing a carbon-carbon double bond by hydrogen peroxide in the presence of the catalyst and the neutral inorganic salt.

16 Claims, No Drawings

METHOD FOR MANUFACTURING AN EPOXY COMPOUND AND METHOD FOR EPOXIDIZING A CARBON—CARBON DOUBLE BOND

TECHNICAL FIELD

The present invention relates to a method for producing an epoxy compound and a method for epoxidizing a carbon-carbon double bond.

BACKGROUND ART

Various epoxy compounds such as α-pinene oxide, limonene oxide, and styrene oxide are important intermediates in the production of chemical products such as flavoring agents. Also, alicyclic epoxy compounds such as β-pinene oxide and camphene oxide are substances important as, for example, encapsulants for electronic materials and cationically curable resins.

As methods for producing such epoxy compounds, patent literature 1 discloses a method for epoxidizing an alicyclic compound having a carbon-carbon double bond by reaction with a percarboxylic acid; and a method for epoxidizing an alicyclic compound having a carbon-carbon double bond by reaction with hydrogen peroxide in the presence of a solvent and a catalyst such as an osmium salt or tungstic acid. However, the former method is problematic in that, for example, peracids are compounds that require careful handling because they are, for example, explosive, and equimolecular wastes are generated after reaction. The latter method is preferable in that hydrogen peroxide generates only water as a by-product but problematic in that the osmium salt is highly toxic.

Patent literature 2 describes a method for producing styrene oxide in which styrene is reacted with peracetic acid in the presence of an alkali metal salt of a weak acid. This method, however, has a problem in that peracetic acid is a compound that requires careful handling because of its explosibility and like properties.

Patent literature 3 describes a method for producing styrene oxide in which styrene is reacted with hydrogen peroxide in the presence of arsenic oxide and 3,5-di-tert-butyl-4-hydroxytoluene. This method, however, is problematic in that arsenic oxide is highly toxic.

Patent literature 4 describes an epoxidizing method in which an alkene such as styrene, indene, cyclohexene, or α-pinene is oxidized by hydrogen peroxide in water or in water and an organic solvent in the presence of a transition metal salt such as manganese sulfate or cobalt acetate, an inorganic promoter such as sodium bicarbonate, and an organic co-promoter such as urea. This method, however, is disadvantageous in that since the method is performed under high dilution conditions, the efficiency for using hydrogen peroxide is poor, and industrial productivity is inferior.

Nonpatent literature 1 describes a method for epoxidizing a terpene such as limonene in an organic solvent such as acetonitrile using a solid catalyst that was prepared by supporting a tungstophosphoric acid derivative represented by $PW_4O_{24}[(C_4H_9)N]_3$ on an ion-exchange resin in the presence of hydrogen peroxide; and a method for epoxidizing α-pinene, 3-carene, 1-phenyl-1-cyclohexene, indene, and the like by hydrogen peroxide in an organic solvent such as benzene using a tungstophosphoric acid derivative represented by $PW_4O_{24}[(C_8H_{17})_3NCH_3]_3$ and aminomethylphosphonic acid as catalysts. However, these methods are problematic in that it is difficult to produce tungstophosphoric acid derivatives and aminomethylphosphonic acid that serve as catalysts.

Nonpatent literature 2 describes a method for epoxidizing olefins such as cyclooctene, cyclohexene, and styrene; and monoterpenes such as α-pinene, limonene, and 3-carene, in a mixed solvent of dichloromethane and acetonitrile, using a Lewis base adduct of a methyltrioxorhenium, by hydrogen peroxide. Nonpatent literature 3 describes a method for epoxidizing styrene, cyclohexene, cyclooctene, and the like by hydrogen peroxide in dichloromethane using methyltrioxorhenium and pyrazole as catalysts. These methods, however, are disadvantageous in that the catalyst methyltrioxorhenium is very expensive and it is difficult to use it in industrial production.

Nonpatent literature 4 describes a method for epoxidizing styrene, cyclooctene, limonene, and the like by hydrogen peroxide in dichloroethane and acetonitrile in the presence of a manganese-porphyrin complex and imidazole. However, it is problematic to industrially carry out this method since an expensive manganese porphyrin complex is used as a catalyst.

Nonpatent literature 5 reports a method for epoxidizing caryophyllene, which has an exomethylene portion, using highly oxidizing m-chloroperbenzoic acid. This method, however, has a problem in that m-chlorobenzoic acid is discharged as a by-product in an amount equimolar to m-chloroperbenzoic acid.

Nonpatent literature 6 reports a method for epoxidizing longifolene, which has an exomethylene portion, by ozonolysis. This method, however, is problematic in that it is industrially difficult to supply ozone at a specific level and after-treat the side product.

Nonpatent literature 7 discloses a method for epoxidizing olefins such as 1-octene, cyclohexene, 2,4,4-trimethyl-2-pentene, and styrene by hydrogen peroxide using quaternary ammonium tetrakis(diperoxotungsto)phosphates as epoxidation catalysts. Although this method performs the reaction in a heterogeneous system that uses benzene or 1,2-dichloroethane as a reaction solvent that is not miscible with water in order to inhibit hydrolysis caused by water generated from hydrogen peroxide, hydrolysis is not sufficiently inhibited. In addition, benzene and the like are toxic and their industrial use is not preferable.

Furthermore, nonpatent literature 8 discloses a method for epoxidizing 1-octene, cyclooctene, a styrene derivative, and the like using hydrogen peroxide in the presence of sodium tungstate, (aminomethyl)phosphonic acid, and methyltrioctylammonium hydrogensulfate. This method, however, is problematic in that it is difficult to obtain (aminomethyl)phosphonic acid and methyltrioctylammonium hydrogensulfate on an industrial scale.

As discussed above, none of the conventionally known methods for epoxidizing organic compounds having a carbon-carbon double bond is regarded as industrially advantageous in terms of safety and economy.

CITATION LIST

Patent Literature

Patent literature 1: JP 2002-80557 A
Patent literature 2: JP 55-149271A
Patent literature 3: JP 55-129276 A
Patent Literature 4: WO 2005/095370

Nonpatent Literature

Nonpatent literature 1: J. Org. Chem. 1999, 64, 7267-7270
Nonpatent literature 2: Tetrahedron 2005, 61, 1069-1075
Nonpatent literature 3: J. Organometallic Chem. 1998, 555, 293-295
Nonpatent literature 4: J. Am. Chem. Soc. 1988, 110, 8462-8470
Nonpatent literature 5: Bull. Soc. Chim. Fr. 1995, 132, 836-842
Nonpatent literature 6: Helv. Chim. Acta 2003, 86, 106-121
Nonpatent literature 7: J. Org. Chem. 1988, 53, 1553-1557
Nonpatent literature 8: Bull. Chem. Soc. Jpn. 1997, 70, 905-915

SUMMARY OF INVENTION

Technical Problem

An object of the present invention is to provide an industrially advantageous method for producing an epoxy compound using a catalyst that is inexpensively obtainable, free of safety concerns, and highly efficient.

Another object of the present invention is to provide a method for efficiently producing an epoxy compound, which is unstable in acid or heat, without causing isomerization or decomposition and without using a harmful substance.

Solution to Problem

The inventors conducted diligent research on a method for epoxidizing a carbon-carbon double bond to solve the above-described problems. As a result, the inventors found that an epoxidizing reaction of a carbon-carbon double bond proceeds efficiently by oxidizing the double bond by hydrogen peroxide in the presence of a neutral inorganic salt as well as a combined catalyst of a tungsten compound, a phosphoric or phosphoric acid, and a surfactant, under mild conditions, for example, at about room temperature. The inventors conducted further research in view of the foregoing finding and accomplished the present invention.

The present invention provides a method for producing an epoxy compound and a method for epoxidizing a carbon-carbon double bond as presented below.

Item 1. A method for producing an epoxy compound, comprising oxidizing a carbon-carbon double bond of an organic compound by hydrogen peroxide in the presence of a neutral inorganic salt and a mixed catalyst of a tungsten compound (a), at least one phosphorus compound selected from the group consisting of phosphoric acids, phosphonic acids, and salts thereof (b), and a surfactant (c).

Item 2. The method for producing an epoxy compound according to item 1, wherein the organic compound having a carbon-carbon double bond is α-pinene or limonene.

Item 3. The method for producing an epoxy compound according to item 1, wherein the organic compound having a carbon-carbon double bond is limonene-1,2-oxide.

Item 4. The method for producing an epoxy compound according to item 1, wherein the organic compound having a carbon-carbon double bond is an alicyclic terpene compound having an exomethylene portion, which is β-pinene, camphene, longifolene, caryophyllene, isocaryophyllene, or caryophyllene-3,4-oxide.

Item 5. The method for producing an epoxy compound according to item 1, wherein the organic compound having a carbon-carbon double bond is 3-carene, α-terpineol, ter-pinene-4-ol, isopulegol, carvone-1,6-oxide, myrcene, sobrerol, γ-terpinene, terpinolene, or 2,4,4-trimethyl-1-pentene.

Item 6. The method for producing an epoxy compound according to item 1, wherein the organic compound having a carbon-carbon double bond is an aromatic compound represented by general formula (I):

[Formula 1]

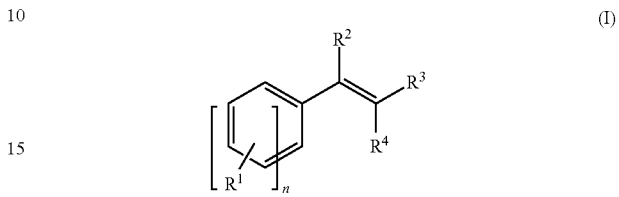

(I)

wherein $R^1$ is an electron donating group or an electron withdrawing group, $R^2$, $R^3$, and $R^4$ are each independently a hydrogen atom or an optionally substituted hydrocarbon group, and n is an integer of 0 to 5, provided that if n is 2 or greater, each $R^1$ may be the same or different.

Item 7. The method for producing an epoxy compound according to item 1, wherein the organic compound having a carbon-carbon double bond is an aromatic compound represented by general formula (II):

[Formula 2]

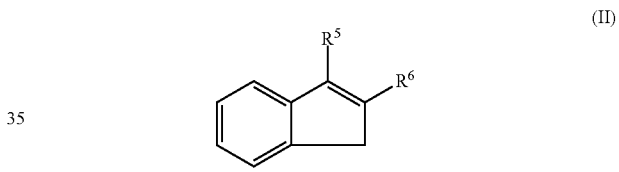

(II)

wherein $R^5$ and $R^6$ are each independently a hydrogen atom or an optionally substituted hydrocarbon group.

Item 8. The method for producing an epoxy compound according to item 1, wherein the tungsten compound (a) is at least one compound selected from the group consisting of tungstic acid, tungsten trioxide, phosphotungstic acid, and sodium tungstate.

Item 9. The method for producing an epoxy compound according to item 1, wherein the phosphorus compound (b) is at least one compound selected from the group consisting of phosphoric acid, phenylphosphonic acid, phosphorous acid, hypophosphorous acid, 2-ethylhexylphosphoric acid, laurylphosphoric acid, and sodium dihydrogenphosphate.

Item 10. The method for producing an epoxy compound according to item 1, wherein the surfactant (c) is at least one compound selected from the group consisting of quaternary ammonium salts and nitrogen ring-containing quaternary ammonium salts.

Item 11. The method for producing an epoxy compound according to item 1, wherein the neutral inorganic salt is a sulfuric acid salt.

Item 12. The method for producing an epoxy compound according to item 11, wherein the sulfuric acid salt is sodium sulfate and/or lithium sulfate.

Item 13. The method for producing an epoxy compound according to item 1, wherein the amount of the hydrogen peroxide used is 0.7 to 5.0 equivalents relative to the carbon-carbon double bond of the organic compound having a carbon-carbon double bond.

Item 14. The method for producing an epoxy compound according to item 1, wherein the amount of the tungsten compound (a) used is 0.0001 to 20 mol % relative to the organic compound having a carbon-carbon double bond.

Item 15. The method for producing an epoxy compound according to item 1, wherein the amount of the phosphorus compound (b) used is 0.0001 to 10 mol % relative to the organic compound having a carbon-carbon double bond.

Item 16. The method for producing an epoxy compound according to item 1, wherein the amount of the surfactant (c) used is 0.0001 to 20 mol % relative to the organic compound having a carbon-carbon double bond.

Item 17. The method for producing an epoxy compound according to item 1, wherein the amount of the neutral inorganic salt used is 1 to 500 mol % relative to the organic compound having a carbon-carbon double bond.

Item 18. A method for epoxidizing a carbon-carbon double bond, comprising oxidizing an organic compound having a carbon-carbon double bond by hydrogen peroxide in the presence of a neutral inorganic salt and a mixed catalyst of a tungsten compound (a), at least one phosphorus compound selected from the group consisting of phosphoric acids, phosphonic acids, and salts thereof (b), and a surfactant (c).

Advantageous Effects of Invention

From the method for producing an epoxy compound and the method for epoxidizing a carbon-carbon double bond of the present invention, the following remarkable effects are obtained.

(1) The following methods are provided: an industrially advantageous method for producing an epoxy compound and method for epoxidizing a carbon-carbon double bond both using a catalyst that is inexpensively obtainable, free of safety concerns, and highly efficient.

(2) An epoxy compound, which is unstable in acid or heat, can be efficiently produced without causing isomerization or decomposition and without using a harmful substance. The by-product of hydrogen peroxide used as an oxidizing agent is water only. Therefore, the production method of the present invention is suitable as a method for industrially producing an epoxy compound.

(3) For example, it is possible to highly selectively synthesize α-pinene oxide or limonene mono- or dioxide in a high yield, while inhibiting the hydrolysis thereof by oxidizing α-pinene or limonene. α-Pinene oxide, limonene monoxide, and limonene dioxide are used in various fields as flavoring agent ingredients, reactive diluents, encapsulants, cleaning agents, polymer modifiers, and the like.

(4) It is possible to highly selectively synthesize limonene dioxide in a high yield, while inhibiting the hydrolysis thereof, by oxidizing limonene monoxide. Limonene dioxide can be used as a reactive diluent, an encapsulant, a cleaning agent, an ingredient of photocurable ink-jet ink, and the like.

(5) It is possible to highly selectively synthesize an alicyclic epoxy compound in a high yield, while inhibiting the isomerization and hydrolysis thereof, by oxidizing an alicyclic compound having an exomethylene portion. Alicyclic epoxy compounds are substances important as encapsulants for electronic materials or cationically curable resins, and used in various fields as flavoring agent ingredients, pharmaceutical and agrochemical intermediates, reactive diluents, cleaning agents, polymer modifiers, and the like.

(6) A terpene compound such as 3-carene, α-terpineol, terpinene-4-ol, isopulegol, carvone-1,6-oxide, β-pinene, myrcene, sobrerol, γ-terpinene or terpinolene, or 2,4,4-trimethyl-1-pentene or the like is oxidized under mild conditions, and the corresponding epoxy compound can be highly selectively synthesized in a high yield while inhibiting the hydrolysis of the epoxy compound obtained. Such epoxy compounds can be used as flavoring agent ingredients, pharmaceutical and agrochemical intermediates, reactive diluents, encapsulants for electronic materials, cationically curable resins, and the like.

(7) It is possible to highly selectively synthesize styrene oxide or a styrene oxide derivative in a high yield by oxidizing styrene or a styrene derivative under mild conditions. Styrene oxide and the like can be used as a flavoring agent ingredient, a polymer stabilizer, an ultraviolet absorber, a pharmaceutical intermediate, and the like.

DESCRIPTION OF EMBODIMENTS

Method for Producing Epoxy Compound

The method for producing an epoxy compound of the present invention comprises oxidizing a carbon-carbon double bond of an organic compound by hydrogen peroxide in the presence of a neutral inorganic salt and a mixed catalyst of a tungsten compound (a), at least one phosphorus compound selected from the group consisting of phosphoric acids, phosphonic acids, and salts thereof (b), and a surfactant (c). Also, the method for producing an epoxy compound of the present invention is an epoxidizing method that oxidizes the carbon-carbon double bond of an organic compound that has a carbon-carbon double bond by hydrogen peroxide in the presence of a neutral inorganic salt using the aforementioned catalyst.

Organic Compound Having Carbon-Carbon Double Bond

The substrate (i.e., a starting compound) in the method for producing an epoxy compound of the present invention is an organic compound having a carbon-carbon double bond. The substrate is not particularly limited as long as it is an organic compound having a carbon-carbon double bond, and various organic compounds such as aliphatic compounds, alicyclic compounds, and aromatic compounds are usable.

Examples of the substrate for the production method of the present invention include monoterpene compounds such as α-pinene and limonene. Known products can be used as α-pinene and limonene without modification.

α-Pinene may be one of (1R)-(+)-α-pinene represented by chemical formula (1) below and (1S)-(−)-α-pinene represented by chemical formula (2) or may be a mixture of these.

[Formula 3]

(1)

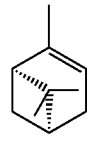

(2)

Limonene may be one of the (1)-limonene represented by chemical formula (3) below and (d)-limonene represented by chemical formula (4) or may be a mixture of these.

[Formula 4]

(3)
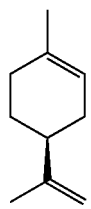

(4)

Another example of the substrate is limonene-1,2-oxide. Known products can be used as this limonene monoxide without modification. Limonene-1,2-oxide may be one of the stereoisomers including the compound represented by chemical formula (5) below, the compound represented by chemical formula (6), the compound represented by chemical formula (7), and the compound represented by chemical formula (8), or may be any mixture of these stereoisomers.

[Formula 5]

(5)
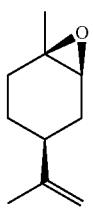

(6)
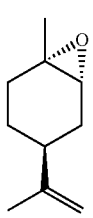

(7)
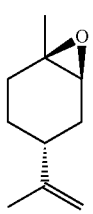

(8)
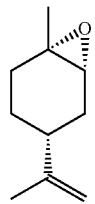

Moreover, examples of the substrate for the present invention include compounds having an exomethylene portion, such as alicyclic compounds having an exomethylene portion, preferably alicyclic terpene compounds. Known products can be used as compounds having an exomethylene portion.

Examples of alicyclic terpene compounds having an exomethylene portion include β-pinene, camphene, β-phellandrene, and like monoterpene compounds; longifolene, caryophyllene, isocaryophyllene, and aromadendrene, and like sesquiterpene compounds; caryophyllene monoxide, phellandrene monoxide, and like terpene epoxy compounds; and the like. Among these compounds, use of β-pinene, camphene, longifolene, caryophyllene, isocaryophyllene, and caryophyllene-3,4-oxide as a substrate enhances, in particular, selectivity and yield.

β-Pinene is represented by chemical formula (9) below.

[Formula 6]

(9)
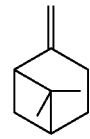

Camphene is represented by chemical formula (10) below.

[Formula 7]

(10)
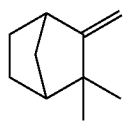

Longifolene is represented by chemical formula (11) below.

[Formula 8]

(11)
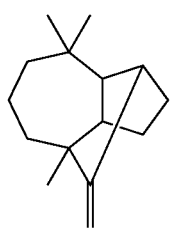

Any of the α-caryophyllene, β-caryophyllene, and isocaryophyllene can be used as caryophyllene. β-Caryophyllene is represented by chemical formula (12) below. Isocaryophyllene is represented by chemical formula (13) below.

[Formula 9]

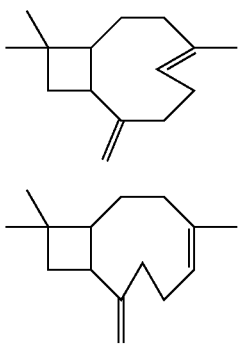

(12)

(13)

Caryophyllene-3,4-oxide is represented by chemical formula (14) below.

[Formula 10]

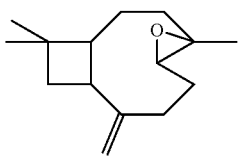

(14)

Examples of the substrate for the production method of the present invention include 3-carene, α-terpineol, terpinene-4-ol, isopulegol, carvone-1,6-oxide, myrcene, carveol, sobrerol, γ-terpinene, terpinolene, ocimene, and like terpene compounds; and 1-octene, cyclohexene, cyclooctene, 2,4,4-trimethyl-1-pentene, and like alkene compounds. Known products can be used as these compounds.

Aromatic compounds having an ethylenic unsaturated double bond can each be used as the substrate for the production method of the present invention. Known such aromatic compounds can be used, and examples include styrenic aromatic compounds represented by general formula (I) below.

[Formula 11]

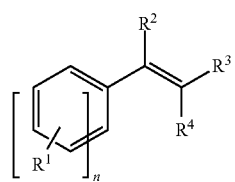

(I)

In general formula (I), $R^1$ is an electron donating group or an electron withdrawing group; $R^2$, $R^3$, and $R^4$ are each independently a hydrogen atom or an optionally substituted hydrocarbon group; n is an integer of 0 to 5; and if n is two or greater, $R^1$ may be the same or different.

Furthermore, examples of substrate aromatic compounds having an ethylenic unsaturated double bond include indenic aromatic compounds represented by general formula (II) below.

[Formula 12]

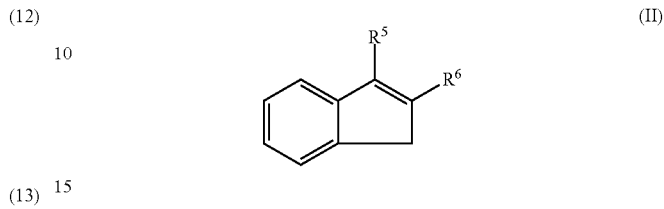

(II)

In general formula (II), $R^5$ and $R^6$ are each independently a hydrogen atom or an optionally substituted hydrocarbon group.

Examples of the electron donating group represented by $R^1$ of general formula (I) include alkyl groups, amino groups, alkoxy groups; and examples of the electron withdrawing group include a fluorine atom, a chlorine atom, a bromine atom, an iodine atom, and like halogen atoms, a trifluoromethyl group, a nitro group, a cyano group, a —$COR^7$ group [with $R^7$ being an alkyl group, an OH group, or an $OR^8$ group (with $R^8$ being an alkyl group)], an alkenyl group, and the like. Examples of the optionally substituted hydrocarbon group represented by $R^2$ to $R^6$ in general formulas (I) and (II) include a methyl group, an ethyl group, a propyl group, an isopropyl group, an n-butyl group, an isobutyl group, a sec-butyl group, a tert-butyl group, a pentyl group, an isopentyl group, a neopentyl group, a tert-pentyl group, a 1-methylpentyl group, a 1-methylheptyl group, an n-hexyl group, an n-octyl group, an n-decyl group, a dodecyl group, a hexadecyl group, an octadecyl group, and like alkyl groups; a vinyl group, an allyl group, a 1-propenyl group, an isopropenyl group, a 1-butenyl group, a 2-butenyl group, a 2-methylallyl group, an ethynyl group, a 2-propenyl group, an octenyl group, a decenyl group, an oleyl group, and like unsaturated chain hydrocarbon groups; a cyclohexyl group, 1-cyclohexenyl, cyclohexylidene, and like alicyclic hydrocarbon groups; a tolyl group (o-, m-, p-), a xylyl group (o-, m-, p-), a cumenyl group (o-, m-, p-), a phenethyl group, an α-methylbenzyl group, a 1-methyl-1-phenylethyl group, a diphenylmethyl group, a benzhydryl group, a styryl group, a cinnamyl group, a benzylidene group, a p-phenylene group, a 4-methyl-m-phenylene group, a 4-biphenylyl group, a 9-anthryl group, a 2-phenantolyl group, and like aromatic hydrocarbon groups.

Examples of the compound represented by general formula (I) include styrene ($R^2$ to $R^4$=hydrogen atoms, n=0), halogen styrene ($R^1$=halogen, $R^2$ to $R^4$=hydrogen atoms, n=1 to 5), alkylstyrene ($R^1$=an alkyl group, $R^2$ to $R^4$=hydrogen atoms, n=1 to 5; or one of $R^2$ to $R^4$ is an alkyl group and the others are hydrogen atoms, two are alkyl groups and the rest is a hydrogen atom, or all three are alkyl groups, n=0), aminostyrene ($R^1$=an amino group, $R^2$ to $R^4$=hydrogen atoms, n=1 to 5), nitrostyrene ($R^1$=a nitro group, $R^2$ to $R^4$=hydrogen atoms, n=1 to 5), cyanostyrene ($R^1$=a cyano group, $R^2$ to $R^4$=hydrogen atoms, n=1 to 5), carboxylstyrene ($R^1$=a carboxyl group, $R^2$ to $R^4$=hydrogen atoms, n=1 to 5), vinylstyrene ($R^1$=a vinyl group, $R^2$ to $R^4$=hydrogen atoms, n=1 to 5), and the like. In particular, in the case where styrene ($R^2$ to $R^4$=hydrogen atoms, n=0), halogenstyrene ($R^1$=halogen, $R^2$ to $R^4$=hydrogen atoms, n=1 to 5), alkylstyrene (one of $R^2$ to $R^4$ is an alkyl group, the others are hydrogen atoms, or two are alkyl groups and the rest is a hydrogen atom, or all three are alkyl groups, n=0), or vinylstyrene ($R^1$=a vinyl group, $R^2$ to $R^4$=hydrogen atoms, n=1 to 5) is used as the substrate, the selectivity for the resulting compound is favorable.

Examples of the compound represented by general formula (II) include indene ($R^5$=H, $R^6$=H), methylindene ($R^5$=H, $R^6$=a methyl group), ethylindene ($R^5$=H, $R^6$=an ethyl group), dimethylindene ($R^5$=a methyl group, $R^6$=a methyl group), and the like. In particular, in the case where indene ($R^5$=H, $R^6$=H) is used as the substrate, the selectivity for the resulting compound is favorable.

Next, the steps of the method for producing an epoxy compound of the present invention will now be described in detail. The production method of the present invention is to synthesize an epoxy compound by oxidizing the carbon-carbon double bond of an organic compound, i.e., a substrate (starting compound), by hydrogen peroxide in the presence of a neutral inorganic salt and a catalyst containing a tungsten compound (a), a specific phosphorus compound (b), and a surfactant (c).

Hydrogen peroxide to be used is not particularly limited, and known products can be used. It is preferable to use hydrogen peroxide in the aqueous solution form due to the handleability. The concentration of an aqueous hydrogen peroxide solution to be used in the reaction is not limited, and an aqueous solution having a concentration of about 1 to about 100 wt % and preferably about 10 to 60 wt % is usually used.

The amount of hydrogen peroxide used is not limited, and it is usually about 0.7 to about 5.0 equivalents, preferably about 0.8 to about 2.5 equivalents, and more preferably about 0.9 to 1.5 equivalents relative to the carbon-carbon double bond contained in the substrate. The amount of hydrogen peroxide used is suitably determined according to the substrate.

In the present invention, a catalyst containing a tungsten compound (a), at least one phosphorus compound selected from the group consisting of phosphoric acids, phosphonic acids, and salts thereof (b), and a surfactant (c) is used.

The tungsten compound (a) is not particularly limited insofar as it is a compound that generates a tungstate anion in water, and known products can be used. Specific examples include tungstic acid, tungsten trioxide, tungsten trisulfide, phosphotungstic acid, and the like; ammonium tungstate, potassium tungstate, sodium tungstate, and like tungstatic acid salts; and the like. Among these examples, tungstic acid, tungsten trioxide, phosphotungstic acid, sodium tungstate, and the like are preferable.

The tungsten compound (a) used may be a single compound or a combination of two or more compounds. The amount thereof used is selected from the range of about 0.0001 to about 20 mol % and preferably about 0.01 to about 10 mol % relative to the substrate.

Phosphoric acids, phosphonic acids, and salts thereof are as follows. Examples of phosphoric acids include phosphoric acid, polyphosphoric acid, pyrophosphoric acid, hexametaphosphoric acid, hypophosphorous acid, phosphorous acid, dodecylphosphoric acid, 2-ethylhexylphosphoric acid, and the like; examples of phosphoric acid salts include sodium phosphate, potassium phosphate, ammonium phosphate, sodium dihydrogenphosphate, disodium hydrogen phosphate, potassium hydrogen phosphate, ammonium hydrogen phosphate, sodium polyphosphate, sodium hexametaphosphate, sodium acid metaphosphate, sodium polyphosphate, sodium pyrophosphate, disodium dihydrogen pyrophosphate, sodium hypophosphite, sodium phosphite, and the like. Examples of phosphonic acids include methylphosphonic acid, ethylphosphonic acid, n-propylphosphonic acid, isopropylphosphonic acid, n-butylphosphonic acid, t-butylphosphonic acid, phenylphosphonic acid, 4-methoxyphenylphosphonic acid, 4-aminophenylphosphonic acid, 1-hydroxyethane-1,1-bis(phosphonic acid), nitrilotris (methylenephosphonic acid), and the like; and examples of phosphonic acid salts include sodium phenylphosphonate and the like. Among these examples, phosphoric acid, phenylphosphonic acid, phosphorous acid, hypophosphorous acid, 2-ethylhexylphosphoric acid, laurylphosphoric acid, sodium dihydrogenphosphate, and the like are preferable.

In the present invention, as the phosphorus compound (b), one compound or a combination of two or more compounds selected from the group consisting of the aforementioned phosphoric acids, phosphonic acids, and salts thereof is used. The amount of the phosphorus compound (b) used is usually selected from the range of about 0.0001 to about 10 mol % and preferably about 0.01 to about 10 mol % relative to the substrate.

Examples of the surfactant (c) include quaternary ammonium salts, nitrogen ring-containing quaternary ammonium salts, quaternary phosphonium salts, macrocyclic polyethers, and the like. Among these examples, quaternary ammonium salts and nitrogen ring-containing quaternary ammonium salts are preferable. Specific examples of quaternary ammonium salts include trioctylmethylammonium chloride, trioctylethylammonium chloride, dilauryldimethylammonium chloride, didecyldimethylammonium chloride, dioleoyldimethylammonium chloride, lauryltrimethylammonium chloride, stearyltrimethylammonium chloride, lauryldimethylbenzylammonium chloride, distearyldimethylammonium chloride, tricaprylmethylammonium chloride, tetrabuthylammonium chloride, benzyltrimethylammonium chloride, benzyltriethylammonium chloride, and the like. Bromides, iodides, sulfites, sulfates, or hydrogensulfates of these may be used.

Examples of nitrogen ring-containing quaternary ammonium salts include quaternary ammonium salts in which the nitrogen ring is composed of a nitrogen-containing heterocycle such as a pyridine ring, a picoline ring, a quinoline ring, an imidazoline ring, or a morpholine ring. Among these examples, a quaternary ammonium compound composed of a pyridine ring is preferable. Specific examples include alkyl ($C_{8-20}$ linear or branched alkyl: the same applies hereinbelow) pyridinium salts (such as N-laurylpyridinium chloride and N-cetylpyridinium chloride), alkylpicolinium salts (such as N-laurylpicolinium chloride), alkylquinolinium chlorides, alkylisoquinolinium chlorides, alkylhydroxyethylimidazoline chlorides, alkylhydroxymorpholine chlorides, and the like. Bromides, iodides, sulfites, sulfates, or hydrogensulfates of these may be used.

The surfactant (c) used may be a single compound or a combination of two or more compounds. The amount thereof used is selected from the range of about 0.0001 to about 20 mol % and preferably about 0.01 to about 10 mol % relative to the substrate.

In the production method of the present invention, the epoxidizing reaction of a carbon-carbon double bond is performed in the presence of the above-described catalyst and a neutral inorganic salt. A preferable example of the neutral inorganic salt is a sulfate. Preferable examples of the sulfate include lithium sulfate, sodium sulfate, potassium sulfate, calcium sulfate, magnesium sulfate, and the like. Sodium sulfate, lithium sulfate, and the like are more preferable. These inorganic salts may be anhydrides or hydrates, or may be mixtures thereof. The neutral inorganic salt used may be a single compound or a combination of two or more compounds. The amount thereof used is selected from the range of about 1 to about 500 mol % and preferably about 10 to about 100 mol % relative to the substrate.

In the production method of the present invention, from the view point of, for example, enhancing the rate of epoxidizing reaction and inhibiting by-product generation, it is preferable that the pH in the reaction system is preferably about 0.1 to about 7.0, and more preferably about 0.5 to about 4.0. In the case where the pH in the reaction system is not within the aforementioned range due to the catalyst composition, the epoxidizing reaction can be carried out using an acid such as sulfuric acid; an acid salt such as a phosphoric acid salt; an alkali metal hydroxide such as sodium hydroxide, or the like to adjust the pH in the reaction system so as to be within the aforementioned range.

In the production method of the present invention, usually, the epoxidizing reaction is performed in a two-phase fluid having an organic phase and an aqueous phase. In the two-phase fluid having an organic phase and an aqueous phase, usually, the catalyst, except for the quaternary ammonium salts, and the neutral inorganic salt and hydrogen peroxide for use in the present invention are water soluble and are in the aqueous phase while the substrate and quaternary ammonium salts are unlikely to dissolve in water and are in the organic phase. An organic solvent may be added to the reaction system as necessary to enhance the reaction rate or to inhibit generation of a reaction by-product. It is preferable to use a hydrophobic solvent such as toluene, xylene, ethyl acetate, cyclohexane, or n-hexane as such an organic solvent. In the case where an organic solvent is used, the amount thereof is about 1 to about 500 mol % and preferably about 10 to about 300 mol % relative to the substrate.

In the production method of the present invention, the reaction temperature is usually about −30 to about 80° C. In the case where the substrate is a compound having an exomethylene portion, the temperature is preferably about 0 to about 80° C. and more preferably about 20 to about 60° C. In the case where the substrate is not a compound having an exomethylene portion, the temperature is preferably about −30 to about 60° C. and more preferably about 0 to 45° C.

The reaction time in the production method of the present invention is suitably determined according to the amount of catalyst used, the reaction temperature, and other factors, and it is usually about 30 minutes to about 24 hours, preferably about 1 to 20 hours, and more preferably about 2 to 12 hours.

To carry out the production method of the present invention, for example, a tungsten compound (a), a phosphorus compound (b), a surfactant (c), a neutral inorganic salt, and an aqueous hydrogen peroxide solution are introduced into a reactor and mixed, a substrate is added, and an epoxidizing reaction is carried out at a specific temperature usually under stirring. The order of addition may be changed as necessary. After the completion of the reaction, the product is separated by a known method, and purified as necessary, to give the desired epoxy compound. For example, the desired epoxy compound can be obtained from the product by distillation. The remaining hydrogen peroxide may be decomposed by an aqueous sodium thiosulphate solution or the like as necessary.

The epoxy compound obtained by the production method of the present invention is α-pinene oxide in the case where α-pinene is used as a substrate. α-Pinene oxide has the stereostructure of any of the compound represented by chemical formula (15), the compound represented by chemical formula (16), the compound represented by chemical formula (17), and the compound represented by chemical formula (18) below. According to the production method of the present invention, usually, a mixture of these stereoisomers is obtained.

[Formula 13]

(15)

(16)

(17)

(18)

In the case where limonene is used as a substrate, limonene-1,2-oxide and limonene dioxide are obtained. In the case where limonene-1,2-oxide is used as a substrate, limonene dioxide is obtained. Limonene-1,2-oxide has the stereostructure of any of the compound represented by chemical formula (5), the compound represented by chemical formula (6), the compound represented by chemical formula (7), and the compound represented by chemical formula (8) above. Limonene dioxide has the stereostructure of any of the compound represented by chemical formula (19), the compound represented by chemical formula (20), the compound represented by chemical formula (21), and the compound represented by chemical formula (22) below. According to the production method of the present invention, usually, a mixture of these stereoisomers is obtained.

[Formula 14]

(19)

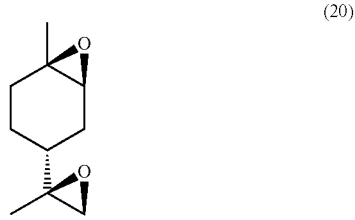

(20)

In the case where β-pinene is used as a substrate, β-pinene oxide is obtained. β-Pinene oxide is represented by chemical formula (23) below.

[Formula 15]

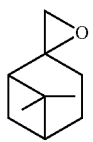
(23)

In the case where camphene is used as a substrate, camphene oxide is obtained. Camphene oxide is represented by chemical formula (24) below.

[Formula 16]

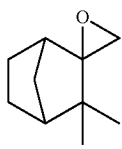
(24)

In the case where longifolene is used as a substrate, longifolene oxide is obtained. Longifolene oxide is represented by chemical formula (25) below.

[Formula 17]

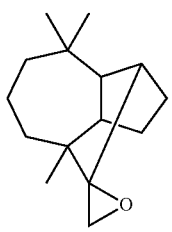
(25)

In the case where caryophyllene or isocaryophyllene is used as a substrate, a mixture of caryophyllene monoxide or caryophyllene dioxide is obtained. Caryophyllene monoxide is usually caryophyllene-3,4-oxide represented by chemical formula (14) above. Caryophyllene dioxide is represented by chemical formula (26) below. In the case where caryophyllene monoxide is used as a substrate, caryophyllene dioxide is obtained.

[Formula 18]

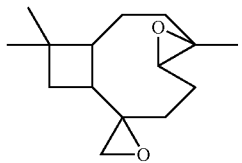
(26)

In the case where a styrenic aromatic compound represented by general formula (I) is used as a starting compound, an aromatic epoxy compound represented by general formula (III) below is obtained.

[Formula 19]

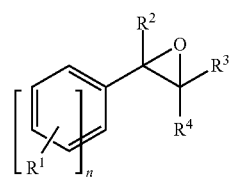
(III)

In general formula (III), $R^1$, $R^2$, $R^3$, $R^4$, and n are as defined above.

In the case where a compound represented by general formula (II) is used as a substrate, an aromatic epoxy compound represented by general formula (IV) below is obtained.

[Formula 20]

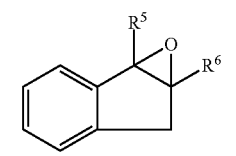
(IV)

In general formula (IV), $R^5$ and $R^6$ are as defined above.

Thus, according to the production method of the present invention, the desired epoxy compound can be highly selectively obtained from a compound having a carbon-carbon double bond in a high degree of conversion and in a high yield. The degree of conversion as used herein refers to "a value obtained by subtracting the gas chromatography (GC) peak area by a gas chromatograph-mass spectrometer of the unreacted starting compound remaining after reaction from the GC peak area of the starting compound before reaction, and expressing the difference in percentage". The selectivity refers to "a value obtained by subtracting the GC peak area of the unreacted starting compound remaining after reaction from the GC peak area of the starting compound before reaction, dividing the GC peak area of the desired epoxy compound by the difference, and expressing the quotient in percentage". The yield refers to "a value expressed in percentage

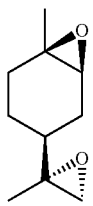
(21)

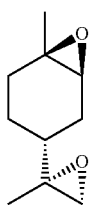
(22)

for the amount of substance of the resulting desired epoxy compound relative to the amount of substance of the substrate".

EXAMPLES

Below, examples and comparative examples are provided to describe the present invention in more detail. The invention, however, is not limited to the examples.

The analyses of the products in the examples and the comparative examples were carried out under the following conditions using a gas chromatograph-mass spectrometer (trade name "7890A/5975C", manufactured by Agilent Technologies).

Column: trade name "HP-5" (manufactured by Agilent Technologies)

Oven temperature: maintained at 50° C. for 5 minutes and increased to 250° C. at a rate of temperature increase of 10° C./min.

Split ratio: "50:1"

Examples of Cases where the Substrate is α-Pinene or Limonene

Example 1

Sodium tungstate dihydrate (19.8 mg, 0.06 mmol), methyltrioctylammonium hydrogen sulfate (27.9 mg, 0.06 mmol), phenylphosphonic acid (4.7 mg, 0.03 mmol), sodium sulfate (128 mg, 0.90 mmol), and a 30 wt % aqueous hydrogen peroxide solution (340 mg, 3.0 mmol) were introduced into a test tube provided with a magnetic stirrer and stirred for 15 minutes, then α-pinene (409 mg, 3.0 mmol) was added at a temperature of 25° C., and an epoxidizing reaction was carried out under stirring for 12 hours. The organic layer separated from the aqueous layer was analyzed by a gas chromatograph-mass spectrometer (hereinafter referred to as a "GC-MS"), showing that the degree of conversion of α-pinene was 92% and the selectivity for α-pinene oxide was 80% (a yield of 74%).

Example 2

A reaction was carried out in the same manner as in Example 1 except that lithium sulfate (231 mg, 2.1 mmol) was added in place of sodium sulfate to carry out the reaction. The degree of conversion of α-pinene was 93% and the selectivity for α-pinene oxide was 84% (a yield of 78%).

Example 3

Sodium tungstate dihydrate (80 mg, 0.24 mmol), methyltrioctylammonium chloride (100 mg, 0.24 mmol), a 42.5 wt % aqueous phosphoric acid solution (14 mg, 0.06 mmol), sodium sulfate (520 mg, 3.66 mmol), a 48.5 wt % diluted aqueous sulfuric acid solution (100 mg, 0.49 mmol), and a 35.5 wt % aqueous hydrogen peroxide solution (1.17 g, 12.2 mmol) were introduced into a test tube provided with a magnetic stirrer and stirred for 30 minutes, α-pinene (1.68 g, 12.2 mmol) was added at a temperature of 25° C., and an epoxidizing reaction was carried out under stirring for 12 hours. The organic layer separated from the aqueous layer was analyzed by a GC-MS, confirming that the degree of conversion of α-pinene was 83% and the selectivity for α-pinene oxide was 94% (a yield of 78%).

Example 4

Sodium tungstate dihydrate (40 mg, 0.12 mmol), methyltrioctylammonium chloride (50 mg, 0.12 mmol), a 42.5 wt % aqueous phosphoric acid solution (3.5 mg, 0.015 mmol), sodium sulfate (520 mg, 3.66 mmol), a 48.5 wt % diluted aqueous sulfuric acid solution (50 mg, 0.24 mmol), and a 35.5 wt % aqueous hydrogen peroxide solution (1.53 g, 15.9 mmol) were introduced into a test tube provided with a magnetic stirrer and stirred for 30 minutes, limonene (1.68 g, 12.2 mmol) was added at a temperature of 25° C., and an epoxidizing reaction was carried out under stirring for 12 hours. The organic layer separated from the aqueous layer was analyzed by a GC-MS, confirming that the degree of conversion of limonene was 99% and the selectivity for limonene-1,2-oxide was 73% (a yield of 72%) and the selectivity for limonene dioxide was 21% (a yield of 20%).

Comparative Example 1

A reaction was carried out under the same conditions as in Example 1 except that sodium sulfate was not used. The degree of conversion of α-pinene was 55% and the selectivity for α-pinene oxide was 2% (a yield of 1%).

Comparative Example 2

A reaction was carried out in the same manner as in Example 1 except that sodium tungstate dihydrate, methyltrioctylammonium hydrogensulfate, and phenylphosphonic acid were not used. The degree of conversion of α-pinene was 2% and the selectivity for α-pinene oxide was 0% (a yield of 0%).

Comparative Example 3

A reaction was carried out in the same manner as in Example 1 except that sodium hydrogen sulfate monohydrate (8.3 mg, 0.06 mmol) was added in place of methyltrioctylammonium hydrogen sulfate. The degree of conversion of α-pinene was 5% and the selectivity for α-pinene oxide was 0% (a yield of 0%).

Comparative Example 4

A reaction was carried out under the same conditions as in Example 3 except that sodium sulfate was not used. The degree of conversion of α-pinene was 23% and the selectivity for α-pinene oxide was 2% (a yield of 1%).

Comparative Example 5

A reaction was carried out under the same conditions as in Example 4 except that sodium sulfate was not used. The degree of conversion of limonene was 77% and the selectivity for limonene-1,2-oxide was 18% (a yield of 13%).

Example 5

Sodium tungstate dihydrate (160 mg, 0.49 mmol), methyltrioctylammonium chloride (197 mg, 0.49 mmol), a 42.5 wt % aqueous phosphoric acid solution (28 mg, 0.12 mmol), sodium sulfate (1.04 g, 7.32 mmol), a 48.5 wt % diluted aqueous sulfuric acid solution (100 mg, 0.49 mmol), and a 35.5 wt % aqueous hydrogen peroxide solution (2.34 g, 24.4 mmol) were introduced into a test tube provided with a magnetic stirrer and stirred for 30 minutes, limonene (1.68 g, 12.2 mmol) was added at a temperature of 25° C., and an epoxidizing reaction was carried out under stirring for 18 hours. The organic layer separated from the aqueous layer was analyzed by a GC-MS, confirming that the degree of conversion of limonene was 100% and the selectivity for limonene-1,2-oxide was 31% (a yield of 30%) and the selectivity for limonene dioxide was 43% (a yield of 43%).

Examples of Cases where the Substrate is Limonene-1,2-Oxide

Example 6

Sodium tungstate dihydrate (80 mg, 0.24 mmol), methyltrioctylammonium chloride (100 mg, 0.24 mmol), a 42.5 wt % aqueous phosphoric acid solution (14 mg, 0.06 mmol), sodium sulfate (520 mg, 3.66 mmol), a 48.5 wt % diluted aqueous sulfuric acid solution (49 mg, 0.24 mmol), and a 35.5 wt % aqueous hydrogen peroxide solution (1.17 g, 12.2 mmol) were introduced into a test tube provided with a magnetic stirrer and stirred for 30 minutes, limonene-1,2-oxide (1.88 g, 12.2 mmol) was added at a temperature of 25° C., and an epoxidizing reaction was carried out under stirring for 19 hours. The organic layer separated from the aqueous layer was analyzed by a GC-MS, confirming that the degree of conversion of limonene-1,2-oxide was 74% and the selectivity for limonene dioxide was 85% (a yield of 63%).

Example 7

A reaction was carried out in the same manner as in Example 5 except that toluene was added as an additive to the reaction system in a proportion of 100 wt % relative to the substrate. The degree of conversion of limonene monoxide was 79% and the selectivity for limonene dioxide was 94% (a yield of 74%).

Example 8

Sodium tungstate dihydrate (120 mg, 0.37 mmol), methyltrioctylammonium chloride (150 mg, 0.37 mmol), a 42.5 wt % aqueous phosphoric acid solution (21 mg, 0.09 mmol), sodium sulfate (520 mg, 3.66 mmol), a 48.5 wt % diluted aqueous sulfuric acid solution (74 mg, 0.37 mmol), and a 35.5 wt % aqueous hydrogen peroxide solution (1.17 g, 12.2 mmol) were introduced into a test tube provided with a magnetic stirrer and stirred for 30 minutes, limonene-1,2-oxide (1.88 g, 12.2 mmol) was added at a temperature of 25° C., and an epoxidizing reaction was carried out under stirring for 9 hours. The organic layer separated from the aqueous layer was analyzed by a GC-MS, confirming that the degree of conversion of limonene-1,2-oxide was 81% and the selectivity for limonene dioxide was 90% (a yield of 73%).

Comparative Example 6

A reaction was carried out under the same conditions as in Example 6 except that sodium sulfate was not used. The degree of conversion of limonene-1,2-oxide was 53% and the selectivity for limonene dioxide was 52% (a yield of 28%).

Comparative Example 7

A reaction was carried out under the same conditions as in Example 8 except that sodium sulfate was not used. The degree of conversion of limonene-1,2-oxide was 59% and the selectivity for limonene dioxide was 57% (a yield of 34%).

Examples of Cases where the Substrate is an Acyclic Terpene Compound Having an Exomethylene Portion Example 9

Sodium tungstate dihydrate (80 mg, 0.24 mmol), methyltrioctylammonium chloride (100 mg, 0.24 mmol), a 42.5 wt % aqueous phosphoric acid solution (56 mg, 0.24 mmol), sodium sulfate (520 mg, 3.66 mmol), a 48.5 wt % diluted aqueous sulfuric acid solution (73.5 mg, 0.36 mmol), and a 35.5 wt % aqueous hydrogen peroxide solution (1.17 g, 12.2 mmol) were introduced into a test tube provided with a magnetic stirrer and stirred for 30 minutes, β-pinene (1.68 g, 12.2 mmol) was added at a temperature of 25° C., and an epoxidizing reaction was carried out under stirring for 7 hours. The organic layer separated from the aqueous layer was analyzed by a GC-MS, confirming that the degree of conversion of β-pinene was 50% and the selectivity for β-pinene oxide was 41% (a yield of 20.5%).

Example 10

Sodium tungstate dihydrate (80 mg, 0.24 mmol), methyltrioctylammonium chloride (100 mg, 0.24 mmol), a 42.5 wt % aqueous phosphoric acid solution (14 mg, 0.06 mmol), sodium sulfate (520 mg, 3.66 mmol), a 48.5 wt % diluted aqueous sulfuric acid solution (100 mg, 0.49 mmol), and a 35.5 wt % aqueous hydrogen peroxide solution (1.17 g, 12.2 mmol) were introduced into a test tube provided with a magnetic stirrer and stirred for 30 minutes, camphene (1.68 g, 12.2 mmol) dissolved in 1.68 g of toluene was added, and an epoxidizing reaction was carried out under stirring at a temperature of 60° C. for 6 hours. The organic layer separated from the aqueous layer was analyzed by a GC-MS, confirming that the degree of conversion of camphene was 89% and the selectivity for camphene oxide was 90% (a yield of 80%).

Example 11

Sodium tungstate dihydrate (80 mg, 0.24 mmol), methyltrioctylammonium chloride (100 mg, 0.24 mmol), a 42.5 wt % aqueous phosphoric acid solution (14 mg, 0.06 mmol), sodium sulfate (520 mg, 3.66 mmol), a 48.5 wt % diluted aqueous sulfuric acid solution (100 mg, 0.49 ramp, and a 35.5 wt % aqueous hydrogen peroxide solution (2.34 g, 24.4 mmol) were introduced into a test tube provided with a magnetic stirrer and stirred for 30 minutes, 6-caryophyllene (2.82 g, 12.2 mmol) was added, and an epoxidizing reaction was carried out under stirring at a temperature of 60° C. for 6 hours. The organic layer separated from the aqueous layer was analyzed by a GC-MS, confirming that the degree of conversion of caryophyllene was 100% and the selectivity for caryophyllene oxide was 88% (46% for 3,4-monoxide and 42% for dioxide).

Example 12

Sodium tungstate dihydrate (80 mg, 0.24 mmol), methyltrioctylammonium chloride (100 mg, 0.24 mmol), a 42.5 wt % aqueous phosphoric acid solution (14 mg, 0.06 mmol), sodium sulfate (520 mg, 3.66 mmol), a 48.5 wt % diluted aqueous sulfuric acid solution (100 mg, 0.49 mmol), and a 35.5 wt % aqueous hydrogen peroxide solution (1.17 g, 12.2 mmol) were introduced into a test tube provided with a magnetic stirrer and stirred for 30 minutes, longifolene (2.73 g, 12.2 mmol) was added, and an epoxidizing reaction was carried out under stirring at a temperature of 60° C. for 12 hours. The organic layer separated from the aqueous layer was analyzed by a GC-MS, confirming that the degree of conversion of longifolene was 68% and the selectivity for longifolene oxide was 97% (a yield of 65%).

Example 13

Sodium tungstate dihydrate (9.9 mg, 0.03 mmol), methyltrioctylammonium chloride (12.1 mg, 0.03 mmol), a 1.0 M aqueous phosphoric acid solution (7.5 µL, 0.0075 mmol), sodium sulfate (256 mg, 1.8 mmol), a 5.0 M aqueous sulfuric acid solution (6.0 µL, 0.03 mmol), and a 30 wt % aqueous hydrogen peroxide solution (680 mg, 6.0 mmol) were introduced into a test tube provided with a magnetic stirrer and stirred for 30 minutes, β-caryophyllene (613 mg, 3.0 mmol) was added, and an epoxidizing reaction was carried out under stirring at a temperature of 60° C. for 12 hours. The organic layer separated from the aqueous layer was analyzed by a GC-MS, confirming that the degree of conversion of caryophyllene was 100%, and the selectivity for caryophyllene-3,4-oxide and dioxide was 19% and 78%, respectively.

Example 14

Sodium tungstate dihydrate (9.9 mg, 0.03 mmol), methyltrioctylammonium chloride (12.1 mg, 0.03 mmol), a 1.0 M aqueous phosphoric acid solution (7.5 µL, 0.0075 mmol), sodium sulfate (256 mg, 1.8 mmol), a 5.0 M aqueous sulfuric acid solution (6.0 µL, 0.03 mmol), and a 30 wt % aqueous hydrogen peroxide solution (340 mg, 3.0 mmol) were introduced into a test tube provided with a magnetic stirrer and stirred for 30 minutes, caryophyllene oxide (661 mg, 3.0 mmol) was added, and an epoxidizing reaction was carried out under stirring at a temperature of 60° C. for 12 hours. The organic layer separated from the aqueous layer was analyzed by a GC-MS, confirming that the degree of conversion of caryophyllene oxide was 85% and the selectivity for caryophyllene dioxide was 100% (a yield of 85%).

Comparative Example 8

A reaction was carried out under the same conditions as in Example 9 except that sodium sulfate was not used. The degree of conversion of β-pinene was 58% and the selectivity for β-pinene oxide was 0% (a yield of 0%).

Comparative Example 9

A reaction was carried out under the same conditions as in Example 10 except that sodium sulfate was not used. The degree of conversion of camphene was 85% and the selectivity for camphene oxide was 10% (a yield of 8.5%).

Comparative Example 10

A reaction was carried out under the same conditions as in Example 11 except that sodium sulfate was not used. The degree of conversion of caryophyllene was 100% and the selectivity for caryophyllene oxide was 71% (51% for 3,4-monoxide and 20% for dioxide).

Comparative Example 11

A reaction was carried out under the same conditions as in Example 12 except that sodium sulfate was not used. The degree of conversion of longifolene was 59% and the selectivity for longifolene oxide was 24% (a yield of 14%).

Comparative Example 12

A reaction was carried out under the same conditions as in Example 13 except that sodium sulfate was not used. The degree of conversion of caryophyllene was 100% and the selectivity for caryophyllene oxide was 42% (35% for 3,4-monoxide and 7% for dioxide).

Example of Cases where the Substrate is a Terpene Compound Such as β-Carene, or 2,4,4-trimethyl-1-oxide Example 15

Sodium tungstate dihydrate (9.90 mg, 0.030 mmol), methyltrioctylammonium chloride (12.1 mg, 0.030 mmol), a 42.5 wt % aqueous phosphoric acid solution (1.73 mg, 0.0075 mmol), sodium sulfate (127.84 mg, 0.90 mmol), a 48.5 wt % diluted aqueous sulfuric acid solution (6.07 mg, 0.030 mmol), and a 35.5 wt % aqueous hydrogen peroxide solution (0.28 g, 3.0 mmol) were introduced into a test tube provided with a magnetic stirrer and stirred for 30 minutes, 3-carene (0.41 g, 3.0 mmol) was added at a temperature of 25° C., and an epoxidizing reaction was carried out under stirring for 12 hours. The organic layer separated from the aqueous layer was analyzed by a GC-MS, confirming that the degree of conversion of 3-carene was 96% and the selectivity for 3-carene oxide was 94% (a yield of 94%).

Example 16

Sodium tungstate dihydrate (9.90 mg, 0.030 mmol), methyltrioctylammonium chloride (12.1 mg, 0.030 mmol), a 42.5 wt % aqueous phosphoric acid solution (1.73 mg, 0.0075 mmol), sodium sulfate (127.84 mg, 0.90 mmol), a 48.5 wt % diluted aqueous sulfuric acid solution (6.07 mg, 0.030 mmol), and a 35.5 wt % aqueous hydrogen peroxide solution (0.28 g, 3.0 mmol) were introduced into a test tube provided with a magnetic stirrer and stirred for 30 minutes, α-terpineol (0.48 g, 3.0 mmol) was added at a temperature of 25° C., and an epoxidizing reaction was carried out under stirring for 12 hours. The organic layer separated from the aqueous layer was analyzed by a GC-MS, confirming that the degree of conversion of α-terpineol was 87% and the selectivity for α-terpineol oxide was 91% (a yield of 79%).

Example 17

Sodium tungstate dihydrate (9.90 mg, 0.030 mmol), methyltrioctylammonium chloride (12.1 mg, 0.030 mmol), a 42.5 wt % aqueous phosphoric acid solution (1.73 mg, 0.0075 mmol), sodium sulfate (127.84 mg, 0.90 mmol), a 48.5 wt % diluted aqueous sulfuric acid solution (6.07 mg, 0.030 mmol), and a 35.5 wt % aqueous hydrogen peroxide solution (0.28 g, 3.0 mmol) were introduced into a test tube provided with a magnetic stirrer and stirred for 30 minutes, terpinene-4-ol (0.48 g, 3.0 mmol) was added at a temperature of 25° C., and an epoxidizing reaction was carried out under stirring for 12 hours. The organic layer separated from the aqueous layer was analyzed by a GC-MS, confirming that the degree of conversion of terpinene-4-ol was 100% and the selectivity for α-terpineol oxide was 98% (a yield of 98%).

Example 18

Sodium tungstate dihydrate (9.90 mg, 0.030 mmol), methyltrioctylammonium chloride (12.1 mg, 0.030 mmol), a 42.5 wt % aqueous phosphoric acid solution (1.73 mg, 0.0075 mmol), sodium sulfate (127.84 mg, 0.90 mmol), a 48.5 wt % diluted aqueous sulfuric acid solution (6.07 mg, 0.030 mmol), and a 35.5 wt % aqueous hydrogen peroxide solution (0.28 g, 3.0 mmol) were introduced into a test tube provided with a magnetic stirrer and stirred for 30 minutes, 2,4,4-trimethyl-1-pentene (0.37 g, 3.0 mmol) was added at a temperature of 25° C., the temperature was increased to 60° C., and an epoxidizing reaction was carried out under stirring for 12 hours. The organic layer separated from the aqueous layer was analyzed by a GC-MS, confirming that the degree of conversion of 2,4,4-trimethyl-1-pentene was 82% and the selectivity for 2,4,4-trimethyl-1-pentene oxide was 97% (a yield of 79%).

Example 19

Sodium tungstate dihydrate (9.90 mg, 0.030 mmol), methyltrioctylammonium chloride (12.1 mg, 0.030 mmol), a 42.5 wt % aqueous phosphoric acid solution (1.73 mg, 0.0075 mmol), sodium sulfate (127.84 mg, 0.90 mmol), a 48.5 wt % diluted aqueous sulfuric acid solution (6.07 mg, 0.030 mmol), and a 35.5 wt % aqueous hydrogen peroxide solution (0.28 g, 3.0 mmol) were introduced into a test tube provided with a magnetic stirrer and stirred for 30 minutes, isopulegol (0.48 g, 3.0 mmol) was added at a temperature of 25° C., the temperature was increased to 40° C., and an epoxidizing reaction was carried out under stirring for 12 hours. The organic layer separated from the aqueous layer was analyzed by a GC-MS, confirming that the degree of conversion of isopulegol was 83% and the selectivity for isopulegol oxide was 100% (a yield of 83%).

Example 20

Sodium tungstate dihydrate (9.90 mg, 0.030 mmol), methyltrioctylammonium chloride (12.1 mg, 0.030 mmol), a 42.5 wt % aqueous phosphoric acid solution (1.73 mg, 0.0075 mmol), sodium sulfate (127.84 mg, 0.90 mmol), a 48.5 wt % diluted aqueous sulfuric acid solution (6.07 mg, 0.030 mmol), and a 35.5 wt % aqueous hydrogen peroxide solution (0.28 g, 3.0 mmol) were introduced into a test tube provided with a magnetic stirrer and stirred for 30 minutes, carvone-1,6-oxide (0.51 g, 3.0 mmol) was added at a temperature of 25° C., the temperature was increased to 50° C., and an epoxidizing reaction was carried out under stirring for 12 hours. The organic layer separated from the aqueous layer was analyzed by a GC-MS, confirming that the degree of conversion of carvone-1,6-oxide was 56% and the selectivity for carvone-1,6-7,8-dioxide was 100% (a yield of 56%).

Example 21

Sodium tungstate dihydrate (80 mg, 0.24 mmol), a 42.5 wt % aqueous phosphoric acid solution (14 mg, 0.06 mmol), sodium sulfate (511 mg, 3.60 mmol), a 48.5 wt % diluted aqueous sulfuric acid solution (48.5 mg, 0.24 mmol), and a 35.5 wt % aqueous hydrogen peroxide solution (1.17 g, 12.2 mmol) were introduced into a test tube provided with a magnetic stirrer and stirred for 30 minutes, methyltrioctylammonium chloride (100 mg, 0.24 mmol) and β-pinene (1.68 g, 12.2 mmol) dissolved in toluene (2.52 g, 27.4 mmol) were added at a temperature of 25° C., the temperature was increased to 40° C., and an epoxidizing reaction was carried out under stirring for 7 hours. The organic layer separated from the aqueous layer was analyzed by a GC-MS, confirming that the degree of conversion of β-pinene was 75% and the selectivity for β-pinene oxide was 91% (a yield of 68.2%).

Example 22

Sodium tungstate dihydrate (40 mg, 0.12 mmol), a 42.5 wt % aqueous phosphoric acid solution (7 mg, 0.03 mmol), sodium sulfate (511 mg, 3.60 mmol), a 48.5 wt % diluted aqueous sulfuric acid solution (24.2 mg, 0.12 mmol), and a 35.5 wt % aqueous hydrogen peroxide solution (1.17 g, 12.2 mmol) were introduced into a test tube provided with a magnetic stirrer and stirred for 30 minutes, methyltrioctylammonium chloride (50 mg, 0.12 mmol) and β-myrcene (1.86 g, 12.2 mmol) were added at a temperature of 25° C., and an epoxidizing reaction was carried out under stirring for 14 hours. The organic layer separated from the aqueous layer was analyzed by a GC-MS, confirming that the degree of conversion of β-myrcene was 77% and the selectivity for myrcene-6,7-monoxide was 100% (a yield of 75%).

Example 23

Sodium tungstate dihydrate (19.6 mg, 0.06 mmol), methyltrioctylammonium chloride (25.4 mg, 0.06 mmol), a 1.0 M aqueous phosphoric acid solution (15.0 μL, 0.0150 mmol), sodium sulfate (130 mg, 0.9 mmol), a 5.0 M aqueous sulfuric acid solution (12.0 μL, 0.06 mmol), and a 30 wt % aqueous hydrogen peroxide solution (329 mg, 2.9 mmol) were introduced into a test tube provided with a magnetic stirrer and stirred for 30 minutes, sobrerol (461 mg, 3.0 mmol) dissolved in 457 mg of toluene was added, and an epoxidizing reaction was carried out at a temperature of 40° C. for 6 hours. The organic layer separated from the aqueous layer was analyzed by a GC-MS, confirming that the degree of conversion of sobrerol was 97% and the selectivity for sobrerol oxide was 100% (a yield of 97%).

Example 24

Sodium tungstate dihydrate (40 mg, 0.12 mmol), a 42.5 wt % aqueous phosphoric acid solution (7 mg, 0.03 mmol), sodium sulfate (511 mg, 3.60 mmol), a 48.5 wt % diluted aqueous sulfuric acid solution (24.2 mg, 0.12 mmol), and a 35.5 wt % aqueous hydrogen peroxide solution (2.34 g, 24.4 mmol) were introduced into a test tube provided with a magnetic stirrer and stirred for 30 minutes, methyltrioctylammonium chloride (50 mg, 0.12 mmol) and γ-terpinene (1.86 g, 12.2 mmol) were added at a temperature of 25° C., and an epoxidizing reaction was carried out under stirring for 14 hours. The organic layer separated from the aqueous layer was analyzed by a GC-MS, confirming that the degree of conversion of γ-terpinene was 100%, and the selectivity for γ-terpinene monoxide and dioxide was 10% and 85%, respectively.

Example 25

Sodium tungstate dihydrate (40 mg, 0.12 mmol), a 42.5 wt % aqueous phosphoric acid solution (7 mg, 0.03 mmol), sodium sulfate (511 mg, 3.60 mmol), a 48.5 wt % diluted aqueous sulfuric acid solution (24.2 mg, 0.12 mmol), and a 35.5 wt % aqueous hydrogen peroxide solution (2.34 g, 24.4 mmol) were introduced into a test tube provided with a magnetic stirrer and stirred for 30 minutes, methyltrioctylammonium chloride (50 mg, 0.12 mmol) and terpinolene (1.86 g, 12.2 mmol) were added at a temperature of 25° C., and an epoxidizing reaction was carried out under stirring for 14 hours. The organic layer separated from the aqueous layer was analyzed by a GC-MS, confirming that the degree of conversion of terpinolene was 62% and the selectivity for terpinolene monoxide was 70% (a yield of 43%).

Comparative Example 13

A reaction was carried out under the same conditions as in Example 15 except that sodium sulfate was not used. The degree of conversion of 3-carene was 97% and the selectivity for 3-carene oxide was 83% (a yield of 81%).

Comparative Example 14

A reaction was carried out under the same conditions as in Example 16 except that sodium sulfate was not used. The degree of conversion of α-terpineol was 86% and the selectivity for α-terpineol oxide was 24% (a yield of 21%).

Comparative Example 15

A reaction was carried out under the same conditions as in Example 17 except that sodium sulfate was not used. The degree of conversion of terpinene-4-ol was 100% and the selectivity for terpinene-4-ol oxide was 46% (a yield of 46%).

Comparative Example 16

A reaction was carried out under the same conditions as in Example 18 except that sodium sulfate was not used. The degree of conversion of 2,4,4-trimethyl-1-pentene was 83% and the selectivity for 2,4,4-trimethyl-1-pentene oxide was 62% (a yield of 52%).

Comparative Example 17

A reaction was carried out under the same conditions as in Example 19 except that sodium sulfate was not used. The degree of conversion of isopulegol was 81% and the selectivity for isopulegol oxide was 10% (a yield of 8%).

Comparative Example 18

A reaction was carried out under the same conditions as in Example 20 except that sodium sulfate was not used. The degree of conversion of carvone-1,6-oxide was 63% and the selectivity for carvone-1,6-7,8-dioxide was 83% (a yield of 52%).

Comparative Example 19

A reaction was carried out under the same conditions as in Example 21 except that sodium sulfate was not used. The degree of conversion of β-pinene was 15% and the selectivity for β-pinene dioxide was 0% (a yield of 0%).

Comparative Example 20

A reaction was carried out under the same conditions as in Example 22 except that sodium sulfate was not used. The degree of conversion of β-myrcene was 13% and the selectivity for myrcene monoxide was 0% (a yield of 0%).

Comparative Example 21

A reaction was carried out under the same conditions as in Example 23 except that sodium sulfate was not used. The degree of conversion of sobrerol was 100% and the selectivity for sobrerol oxide was 70% (a yield of 70%).

Comparative Example 22

A reaction was carried out under the same conditions as in Example 24 except that sodium sulfate was not used. The degree of conversion of γ-terpinene was 43%, and the selectivity for γ-terpinene monoxide and dioxide was 27% and 9%, respectively.

Comparative Example 23

A reaction was carried out under the same conditions as in Example 25 except that sodium sulfate was not used. The degree of conversion of terpinolene was 77% and the selectivity for terpinolene monoxide was 44% (a yield of 34%).

Example of Cases where the Substrate is an Aromatic Compound Having a Carbon-Carbon Double Bond Example 26

Sodium tungstate dihydrate (80 mg, 0.24 mmol), methyltrioctylammonium chloride (100 mg, 0.24 mmol), a 42.5 wt % aqueous phosphoric acid solution (28 mg, 0.12 mmol), sodium sulfate (520 mg, 3.66 mmol), a 48.5 wt % diluted aqueous sulfuric acid solution (98 mg, 0.48 mmol), and a 35.5 wt % aqueous hydrogen peroxide solution (1.17 g, 12.2 mmol) were introduced into a test tube provided with a magnetic stirrer and stirred for 30 minutes, styrene (1.27 g, 12.2 mmol) was added at a temperature of 25° C., and an epoxidizing reaction was carried out under stirring for 6 hours. The organic layer separated from the aqueous layer was analyzed by a GC-MS, confirming that the degree of conversion of styrene was 86% and the selectivity for styrene oxide was 93% (a yield of 80%).

Example 27

Sodium tungstate dihydrate (19.8 mg, 0.06 mmol), methyltrioctylammonium chloride (24.2 mg, 0.06 mmol), a 5.0 M aqueous phosphoric acid solution (3 µL, 0.0015 mmol), sodium sulfate (170 mg, 1.2 mmol), a 5.0 M aqueous sulfuric acid solution (14 µL, 0.07 mmol), and a 30 wt % aqueous hydrogen peroxide solution (340 mg, 3.0 mmol) were introduced into a test tube provided with a magnetic stirrer and stirred for 1 minute, styrene (312 mg, 3.0 mmol) was added at a temperature of 25° C., and an epoxidizing reaction was carried out under stirring for 10 hours. The organic layer separated from the aqueous layer was analyzed by a GC-MS, confirming that the degree of conversion of styrene was 94% and the selectivity for styrene oxide was 90% (a yield of 85%).

Comparative Example 24

A reaction was carried out under the same conditions as in Example 26 except that sodium sulfate was not used. The degree of conversion of styrene was 37% and the selectivity for styrene oxide was 1.2% (a yield of 0.4%).

Comparative Example 25

A reaction was carried out under the same conditions as in Example 27 except that phosphoric acid was not used. The degree of conversion of styrene was 29% and the selectivity for styrene oxide was 91% (a yield of 26%).

Comparative Example 26

A reaction was carried out under the same conditions as in Example 27 except that methyltrioctylammonium chloride and sulfuric acid were not added. The degree of conversion of styrene was 0% and the selectivity for styrene oxide was 0% (a yield of 0%).

Comparative Example 27

A reaction was carried out under the same conditions as in Example 27 except that sodium tungstate was not used. The degree of conversion of styrene was 0% and the selectivity for styrene oxide was 0% (a yield of 0%).

Example 28

A reaction was carried out in the same manner as in Example 26 except that indene was used in place of styrene. The degree of conversion of indene was 62% and the selectivity for indene oxide was 81% (a yield of 50%).

Example 29

A reaction was carried out under the same conditions as in Example 27 except that 4-fluorostyrene (366 mg, 3.0 mmol) was used as a substrate in place of styrene. The degree of conversion of 4-fluorostyrene was 88% and the selectivity for 4-fluorostyrene oxide was 84% (a yield of 74%).

Example 30

A reaction was carried out under the same conditions as in Example 27 except that 4-chlorostyrene (415 mg, 3.0 mmol) was used as a substrate in place of styrene. The degree of conversion of 4-chlorostyrene was 97% and the selectivity for 4-chlorostyrene oxide was 91% (a yield of 88%).

Example 31

A reaction was carried out under the same conditions as in Example 27 except that 4-bromostyrene (549 mg, 3.0 mmol) was used as a substrate in place of styrene. The degree of conversion of 4-bromostyrene was 81% and the selectivity for 4-bromostyrene oxide was 100% (a yield of 81%).

Example 32

A reaction was carried out under the same conditions as in Example 27 except that 4-nitrostyrene (447 mg, 3.0 mmol) was used as a substrate in place of styrene. The degree of conversion of 4-nitrostyrene was 63% and the selectivity for 4-chlorostyrene oxide was 90% (a yield of 57%).

Example 33

A reaction was carried out under the same conditions as in Example 27 except that α-methylstyrene (355 mg, 3.0 mmol) was used as a substrate in place of styrene. The degree of conversion of α-methylstyrene was 94% and the selectivity for α-methylstyrene oxide was 90% (a yield of 85%).

Example 34

A reaction was carried out under the same conditions as in Example 27 except that trans-β-methylstyrene (355 mg, 3.0 mmol) was used as a substrate in place of styrene. The degree of conversion of trans-β-methylstyrene was 79% and the selectivity for trans-β-methylstyrene oxide was 90% (a yield of 71%).

Example 35

A reaction was carried out under the same conditions as in Example 27 except that cis-β-methylstyrene (355 mg, 3.0 mmol) was used as a substrate in place of styrene. The degree of conversion of cis-β-methylstyrene was 97% and the selectivity for α-methylstyrene oxide was 96% (a yield of 93%).

Comparative Example 28

A reaction was carried out under the same conditions as in Example 28 except that sodium sulfate was not used. The degree of conversion of indene was 23% and the selectivity for indene oxide was 6% (a yield of 1.3%).

Comparative Example 29

A reaction was carried out under the same conditions as in Example 29 except that sodium sulfate was not used. The degree of conversion of 3-fluorostyrene was 43% and the selectivity for 4-fluorostyrene oxide was 0% (a yield of 0%).

Comparative Example 30

A reaction was carried out under the same conditions as in Example 30 except that sodium sulfate was not used. The degree of conversion of 3-chlorostyrene was 77% and the selectivity for 4-chlorostyrene oxide was 30% (a yield of 23%).

Comparative Example 31

A reaction was carried out under the same conditions as in Example 31 except that sodium sulfate was not used. The degree of conversion of 3-bromostyrene was 51% and the selectivity for 4-bromostyrene oxide was 53% (a yield of 27%).

Comparative Example 32

A reaction was carried out under the same conditions as in Example 32 except that sodium sulfate was not used. The degree of conversion of 3-nitrostyrene was 60% and the selectivity for 4-nitrostyrene oxide was 64% (a yield of 38%).

Comparative Example 33

A reaction was carried out under the same conditions as in Example 33 except that sodium sulfate was not used. The degree of conversion of α-methylstyrene was 83% and the selectivity for α-methylstyrene oxide was 8% (a yield of 7%).

Comparative Example 34

A reaction was carried out under the same conditions as in Example 34 except that sodium sulfate was not used. The degree of conversion of trans-β-methylstyrene was 67% and the selectivity for trans-β-methylstyrene oxide was 39% (a yield of 27%).

INDUSTRIAL APPLICABILITY

The present invention can be suitably used in a broad range of industrial fields as flavoring agents, pharmaceuticals, agrochemicals, reactive diluents, encapsulants, cleaning agents, polymer modifiers, ink, resin, ultraviolet absorbers, and the like.

The invention claimed is:

1. A method for producing an epoxy compound, comprising oxidizing a carbon-carbon double bond of an organic compound by hydrogen peroxide in the presence of a neutral inorganic salt and a mixed catalyst of a tungsten compound (a), at least one phosphorus compound selected from the group consisting of phosphoric acids, phosphonic acids, and salts thereof (b), and a surfactant (c),
wherein the neutral inorganic salt is in a concentration of 10 to 100 mol % relative to the organic compound having a carbon-carbon double bond.

2. The method for producing an epoxy compound according to claim 1, wherein the organic compound having a carbon-carbon double bond is α-pinene or limonene.

3. The method for producing an epoxy compound according to claim 1, wherein the organic compound having a carbon-carbon double bond is limonene-1,2-oxide.

4. The method for producing an epoxy compound according to claim 1, wherein the organic compound having a carbon-carbon double bond is an alicyclic terpene compound having an exomethylene portion, which is β-pinene, camphene, longifolene, caryophyllene, isocaryophyllene, or caryophyllene-3,4-oxide.

5. The method for producing an epoxy compound according to claim 1, wherein the organic compound having a carbon-carbon double bond is 3-carene, α-terpineol, terpinene-4-ol, isopulegol, carvone-1,6-oxide, myrcene, sobrerol, γ-terpinene, terpinolene, or 2,4,4-trimethyl-1-pentene.

6. The method for producing an epoxy compound according to claim 1, wherein the organic compound having a carbon-carbon double bond is an aromatic compound represented by formula (I):

[Formula 1]

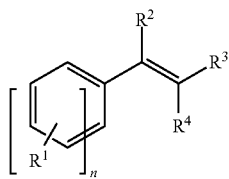

(I)

wherein $R^1$ is an electron donating group or an electron withdrawing group, $R^2$, $R^3$, and $R^4$ are each independently a hydrogen atom or a hydrocarbon group, and n is an integer of 0 to 5, provided that if n is 2 or greater, each $R^1$ may be the same or different.

7. The method for producing an epoxy compound according to claim 1, wherein the organic compound having a carbon-carbon double bond is an aromatic compound represented by formula (II):

[Formula 2]

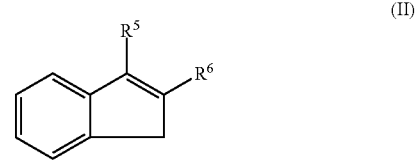

(II)

wherein $R^5$ and $R^6$ are each independently a hydrogen atom or a hydrocarbon group.

8. The method for producing an epoxy compound according to claim 1, wherein the tungsten compound (a) is at least one compound selected from the group consisting of tungstic acid, tungsten trioxide, phosphotungstic acid, and sodium tungstate.

9. The method for producing an epoxy compound according to claim 1, wherein the phosphorus compound (b) is at least one compound selected from the group consisting of phosphoric acid, phenylphosphonic acid, phosphorous acid, hypophosphorous acid, 2-ethylhexylphosphoric acid, laurylphosphoric acid, and sodium dihydrogenphosphate.

10. The method for producing an epoxy compound according to claim 1, wherein the surfactant (c) is at least one compound selected from the group consisting of quaternary ammonium salts and nitrogen ring-containing quaternary ammonium salts.

11. The method for producing an epoxy compound according to claim 1, wherein the neutral inorganic salt is a sulfuric acid salt.

12. The method for producing an epoxy compound according to claim 11, wherein the sulfuric acid salt is sodium sulfate and/or lithium sulfate.

13. The method for producing an epoxy compound according to claim 1, wherein the amount of the hydrogen peroxide used is 0.7 to 5.0 equivalents relative to the carbon-carbon double bond of the organic compound having a carbon-carbon double bond.

14. The method for producing an epoxy compound according to claim 1, wherein the amount of the tungsten compound (a) used is 0.0001 to 20 mol % relative to the organic compound having a carbon-carbon double bond.

15. The method for producing an epoxy compound according to claim 1, wherein the amount of the phosphorus compound (b) used is 0.0001 to 10 mol % relative to the organic compound having a carbon-carbon double bond.

16. The method for producing an epoxy compound according to claim 1, wherein the amount of the surfactant (c) used is 0.0001 to 20 mol % relative to the organic compound having a carbon-carbon double bond.

* * * * *